(12) United States Patent
Tagawa

(10) Patent No.: US 7,114,807 B2
(45) Date of Patent: Oct. 3, 2006

(54) WINDSHIELD EYEGLASSES, WINDSHIELDS FOR EYEGLASSES, AND METHOD FOR WINDSHIELDING IN EYEGLASSES

(75) Inventor: Masahiro Tagawa, Fukui (JP)

(73) Assignee: Madmix Japan Co., Ltd., Fukui (JP)

( * ) Notice: Subject to any disclaimer, the term of this patent is extended or adjusted under 35 U.S.C. 154(b) by 317 days.

(21) Appl. No.: 10/450,537

(22) PCT Filed: Dec. 27, 2001

(86) PCT No.: PCT/JP01/11603
§ 371 (c)(1),
(2), (4) Date: Jun. 20, 2003

(87) PCT Pub. No.: WO02/052334
PCT Pub. Date: Jul. 4, 2002

(65) Prior Publication Data
US 2004/0051839 A1 Mar. 18, 2004

(30) Foreign Application Priority Data
Dec. 27, 2000 (JP) .............................. 2000-396993

(51) Int. Cl.
G02C 5/08 (2006.01)
(52) U.S. Cl. .............................. 351/62; 351/158; 2/435
(58) Field of Classification Search .................. 351/41, 351/43, 44, 158, 62; 2/426, 427, 428, 431, 2/435
See application file for complete search history.

(56) References Cited

U.S. PATENT DOCUMENTS 4,405,212 A * 9/1983 Cooper ..................... 351/43
5,423,092 A 6/1995 Kawai

FOREIGN PATENT DOCUMENTS

JP 4-75019 3/1992

* cited by examiner

Primary Examiner—Hung Xuan Dang
(74) Attorney, Agent, or Firm—Armstrong, Kratz, Quintos, Hanson & Brooks, LLP.

(57) ABSTRACT

A pair of windshield eyeglasses (101) comprises: lenses (106) and a frame (102) for holding the lenses. Each of the lenses or the frame includes an edge formed with a windshield (107) for sealing a gap between the edge and a face of a user. The windshield extends from the edge and ranges from laterally inward side of the face to an upper intermediate portion and to a lower intermediate portion of the frame.

By providing the windshield, the airflow along the user's face is changed to flow along the outside of the windshield. Therefore, the airflow along the face is prevented from entering between the eyeglass inner surface and the user's face. In particular, the airflow is effectively prevented from affecting the eyes from medial angles of eyes toward lateral angles of eyes. This eliminates interference with the natural flow of tears on the eye surface, making it possible to effectively prevent drying and inflammation in the eyes, or prevent foreign materials from coming into the eyes.

9 Claims, 19 Drawing Sheets

WINDSHIELD EYEGLASSES, WINDSHIELDS FOR EYEGLASSES, AND METHOD FOR WINDSHIELDING IN EYEGLASSES

TECHNICAL FIELD

The present invention relates to windshield eyeglasses, windshields for eyeglasses, and a method for wind shielding in eyeglasses. More specifically, the present invention relates to windshield eyeglasses capable of preventing airflow from coming sideways to behind the eyeglasses during a ride on a motorcycle, sports activities such as skiing, and so on.

BACKGROUND ART

Sunglasses are often used when riding on motorcycles, driving convertibles or playing outdoor sports such as skiing. Sunglasses protect the eyes not only from ultraviolet rays but also from being hit directly by airflow during high-speed moving.

There is another option available, in the form of goggles. The frame or lenses of goggles have their perimeters completely enclosed by a wall that prevents wind and dirt from coming in, there is no airflow coming into the space enclosed by the lenses and the frame. This prevents wind and airflow from affecting the eyes.

Human eyes are constantly lubricated with tears supplied by lachrymal glands. Lachrymal glands are located above and laterally outward of respective eyeballs, i.e. above respective lateral angles of eyes. Therefore, tears flow above the lateral angles of eyes toward the medial angles of eyes, lubricating and protecting the eyes from various stimuli.

Now, when moving forward at a high speed, with the face oriented ahead, the face is hit by a flow of air. The airflow is divided by the nose ridge in right and left directions, and then continues to flow along the face. When eyeglasses are worn, the airflow along the face comes into gaps between the eyeglasses and the face, and flows over the eyeball surfaces in directions against the flow of tears. This interferes the flow of tears, and dries the eyes even if eyeglasses are worn. Also, this often causes inflammation in the eyes. For this reason, conventional sunglasses and eyeglasses often do not work as a windshield when riding on motorcycles, skiing, and so on.

In an attempt to alleviate the problem, some eyeglasses are designed so that the lenses and the frame will be closer to the face. However, placing the lenses and the frame simply closer to the face does not eliminate the gap between the face and the lenses. Therefore, this does not prevent the airflow along the face from coming sideways behind the eyeglasses. Further, if the lenses are placed too close to the face, lens surfaces make contact with user's cilia, and are often smudged or otherwise damaged.

Goggles, which have surrounding walls capable of sealing entirely around the eyes, can perfectly prevent the airflow along the face from entering the inner space behind the eyeglasses. However, due to the surrounding wall design, the user's face looks so different that there is resistance in people to wearing goggles in the same manner as they wear eyeglasses in their daily lives. Further, due to the need for the surrounding wall to be fitted to the contours of the face, goggles must be constantly pressed against the face by means of a rubber band for example. For this reason, it is troublesome to wear goggles. Still further, it is difficult to incorporate nicely looking outer design in goggles. In addition, the lenses of goggles, which are isolated from the outer atmosphere, will easily be clouded when there is a temperature difference between inside and outside of the goggles, often making it difficult to see clearly and widely enough.

Sometimes, ordinary eyeglasses mounted with prescription lenses are converted to sunglasses by providing color coating on the prescription lenses or by attaching a colored plate over the prescription lenses for shielding ultraviolet rays.

However, the colored plate is placed over the outer surface of the lenses. This interferes with originally designed looks, and reduces the esthetic value of the eyeglasses. Further, the colored plate, which is detachable from the lens outer surface, does not have a very firm hold in place, and therefore can be vibrated by strong airflow or potentially blown off the eyeglass frame.

DISCLOSURE OF THE INVENTION

A pair of windshield eyeglasses according to the present invention comprises: lenses and a frame for holding the lenses. Each of the lenses or the frame includes an edge formed with a windshield for sealing a gap between the edge and a face of a user. The windshield extends from the edge and ranges from laterally inward side of the face to an upper intermediate portion and to a lower intermediate portion of the frame.

The windshield provides continuous sealing on the laterally inward side of, as well as above and below, the eyes of the user, over the range as described above. By providing the windshield, the airflow along the user's face is changed to flow along the outside of the windshield. Therefore, the airflow along the face is prevented from entering between the eyeglass inner surface and the user's face. In particular, the airflow is effectively prevented from affecting the eyes from medial angles of the eyes toward lateral angles of the eyes. This eliminates interference with the natural flow of tears on the eye surface, making it possible to effectively prevent drying and inflammation in the eyes, or prevent foreign materials from coming into the eyes. By providing the windshield as far as above and below, or beyond the lateral angles of eyes, it becomes possible to effectively prevent adverse effects from the airflow during movement. In addition, the windshield eyeglasses according to the present invention do not seal entirely around the lenses as do the goggles, and so are less susceptible to clouding of the lenses.

Further, the windshield is formed inside an ordinary eyeglass frame and therefore, is not likely to affect the appearance of the eyeglasses or to decrease esthetic value of the eyeglass design. Further, the windshield eyeglasses can be worn just as conventionally by means of temples, which offer handiness to users. Further, since it is possible to provide a large distance between the lenses and the user's face, it is unlikely that the cilia contact and smudge or otherwise damage the lenses.

As far as it is possible to prevent airflow from coming between the lens inner surface and the user's face, the right and the left windshield may be provided independently from each other or continuously with each other.

There is no specific limitation to the shape of the windshield. For example, the windshield can have a tapered shape with its height gradually decreasing from the facially inward side of the medial angles of eyes toward the lateral angles of eyes. When the windshield is given the tapered shape, any unnatural feeling is eliminated when wearing the glasses. By providing the tapered windshield, it becomes possible to make the eyeglasses fit the facial contours of most people. Further, since the windshield does not provide an enclosure entirely around the eyes, unlike goggles, the windshield does not make the user's face very unrecognizable.

As disclosed in Claim 2, the windshield can include a right and a left windshield portions for surrounding the right and left eyes respectively, ranging from the laterally inward side of the medial angles of the eyes to above and below the lateral angles of the eyes. When the windshield is provided as far as above and below the lateral angles of the eyes, the flow of air which affects the eyes can be sufficiently blocked. It should be noted here that the windshield may go beyond the above and below the lateral angles of eyes, depending on the shape of eyeglass frame. For example, if the right and the left rims are rectangular, the windshield can be along the inward edge as well as along the upper and the lower edges of each rim. Depending on purposes of eyeglasses and the force of airflow that hits the face, the windshield may not need to be extended as far as the lateral angles of the eyes, yet will offer sufficient effect.

As disclosed in Claim 3, the right and the left windshield portions can be formed integrally and continuously with each other. It should be noted here that even when the right and the left windshield portions are formed integrally and continuously, it is preferable that a partition wall is provided between the right and the left windshield portions in order to block airflow which would otherwise move laterally of the face behind the windshield.

As described in Claim 4, the lenses corresponding to the right and the left eyes respectively can be provided in the form of a single piece, and the windshield can be formed integrally along the piece or the frame which holds the piece.

There is no specific limitation to the shape of the eyeglasses. The present invention is applicable not only to eyeglasses having rims for holding the lenses on the peripheral edges but also to those having the two lenses connected directly with each other via a bridge, as well as to those having the two lenses directly connected to the temples. There is no specific limitation to the shape of the rims, either. Namely, the present invention is applicable not only to eyeglasses having rims surrounding the entire lens peripheral edges but also to those having rims holding the lenses only on the upper edges. Further, there is no limitation to the purpose of the eyeglasses. Specifically, the present invention is applicable to sunglasses, prescription eyeglasses, eye-protection glasses, and many other kinds of eyeglasses.

There is no limitation to materials or methods for manufacturing the eyeglass frame. The present invention is applicable to frames made of resin and those made of metals.

An invention disclosed in Claim 5 is the windshield eyeglasses in which the windshield is formed integrally with nose pads. Airflow which affects the eyes often comes in from near the nose pads to between the face and the eyeglasses. For this reason, formation of the windshield portion integrally with the nose pads can be effective. Further, formation of the windshield portion integrally with the nose pads makes manufacture of the eyeglasses easy.

An invention disclosed in Claim 6 is the windshield eyeglasses in which the frame is formed of colored resin whereas the windshield is formed of transparent resin. The frame and the windshield are formed integrally with each other, and the frame and the windshield share a border region, along which a bordering groove is formed.

The windshield formed of transparent resin makes the windshield less noticeable, alleviating an impression that the frame main body is thick. This helps improve esthetic design. Further, the windshield allows light to come inside the space behind the eyeglasses, creating a look and feel similar to those of conventional eyeglass frames.

The bordering groove reduces visual impact on the looks of the windshield. Further, if the bordering groove is provided and the windshield is formed of transparent resin, light refracts in the bordering groove, creating a prism effect which represents a unique frame design unfound before. The bordering groove is preferably formed at least along the upper edge of the windshield, since the upper edge of the windshield is the most eye-catching area.

The windshield can be formed integrally with the lenses or the frame, or the windshield and the frame are formed of different materials and connected to each other by adhesive for example. As disclosed in Claim 7, the windshield formed of elastic resin can be bonded to the frame made of hard resin or metal.

Further, as disclosed in Claim 8, the eyeglasses can further include a middle frame between an outer perimeter of each lens and the frame which holds the lenses. The windshield is provided on the middle frame.

By providing the windshield via the middle frame, it becomes possible to manufacture the lenses and the frame in exactly the same way as conventionally. In addition, it becomes easy to manufacture the windshield in varieties of shapes and sizes.

According to inventions disclosed in Claim 9 through Claim 15, the windshield is detachable from the lenses and/or the frame.

An invention disclosed in Claim 9 offers a pair of windshield eyeglasses comprising lenses and a frame for holding the lenses. Each of the lenses or the frame includes an edge formed with a windshield for sealing gaps between the edge and the face of a user. The windshield ranges from the laterally inward side of the face to an upper intermediate portion and to a lower intermediate portion of the frame. The windshield is provided on the lenses and/or the frame, and detachable therefrom.

The detachable windshield allows attaching the windshield only when needed. This feature remarkably improves usability of the eyeglasses. Further, since the eyeglasses less the windshield can be conventional eyeglasses, a lot of design advantages can be enjoyed. Further, it becomes possible to manufacture various kinds of the windshield to match different features of the users. This enables to offer windshields which have highly effective wind shielding capabilities.

There is no limitation to the shape of the eyeglasses to which the windshield can be attached, as is the case in the inventions disclosed in Claim 1 through Claim 8.

There is no limitation either, to the shape of the windshield. For example, as disclosed in Claim 10, the windshield can include a right and a left windshield portions for surrounding the right and left eyes respectively, ranging from the laterally inward side of the medial angles of the eyes to above and below the lateral angles of the eyes. Also, each of the right and the left windshield portions can be detachable with respect to the lenses and/or the frame. Further, the windshield can be an integration of a right and a left windshield portions, and the integrated windshield can be detachably provided onto the frame.

As disclosed in Claim 11, the windshield can be formed integrally with nose pads. By forming the nose pads integrally with the windshield and changing nose pad design, it becomes possible to offer a wide variety of selections for a windshield which fits the face of the user.

Means for detachably providing the windshield can be many. For example, as disclosed in Claim 12, the windshield can be detachably connected to the lenses and/or the frame by magnetic or elastic connecting means. Further, the frame can be provided with a groove or a ridge, to be detachably engaged by a corresponding ridge or groove formed of elastic resin on the windshield.

There is no specific limitation to the place where the windshield is connected to the lenses and/or the frame. The connection may be made directly to the edge of the lenses or rims which holds the lenses, to the bridge or to the nose pads.

When the windshield is made detachable with respect to the lenses and/or the frame, it is preferable that an arrangement is made for not allowing a gap between the windshield and the lenses and/or the frame. For example, as disclosed in Claim 13, the lenses and/or the frame can be formed integrally with an extension for surrounding an outer perimeter of the windshield. By providing the extension, the edge of the windshield can be fitted inside the extension. This covers up any gap between the windshield and the frame, thereby preventing airflow from coming in behind the eyeglasses.

As disclosed in Claim 14, the extension can be made on a middle frame provided between an outer perimeter of each lens and the frame which holds the lenses. By providing the extension in the middle frame, it becomes possible to manufacture the lens and the frame in exactly the same way as conventionally. In addition, the extension can be varied to fit different shapes of the windshield.

An invention disclosed in Claim 15 is the windshield eyeglasses in which the eyeglasses include a middle frame between an outer perimeter of each lens and the frame which holds the lenses. The windshield is detachably connected to the middle frame.

With this arrangement, it becomes possible to manufacture the lens and the frame in exactly the same way as conventionally. In addition, it becomes possible to select the windshield from a variety of shapes. The middle frame can be formed with a continuous ridge for example, so that the windshield made of elastic resin can be detachably mounted.

Inventions disclosed in Claim 16 through Claim 18 relate to the windshield itself.

A windshield according to the invention in Claim 16 comprises: a right and a left windshield portions to be placed along an edge of the eyeglass lenses or frame which holds the lenses, ranging from the laterally inward side of the medial angles of the eyes to above and below the lateral angles of the eyes; and connecting means for connecting the windshield detachably to the lenses and/or the frame.

There is no specific limitation to the means for detachable connection. The connecting means can be provided on the lenses and/or the frame, or arrangements may be made so that conventional lenses and frames can be used for the connection. Further, the nose pads and related parts may be used for the connection.

An invention disclosed in Claim 17 is the windshield for a pair of eyeglasses. The right and the left windshield portion are independent from each other, the windshield portions are connected to each other by a connecting portion to be placed at a laterally central region of the user's face, and the connecting portion is attachable to one or more places of the lenses, the frame or nose pads.

The connecting portion can be formed of the same material as of the windshield and formed integrally with the windshield. Alternatively, the windshield portions may be connected together by a different material.

An invention disclosed in Claim 18 is a pair of windshield eyeglasses comprising lenses and a frame for holding the lenses. Each of the lenses or the frame includes an edge formed with a windshield for sealing a gap between the edge and the face of a user. The windshield extends from the edge and ranges from the laterally inward side of the face to an upper intermediate portion and to a lower intermediate portion of the frame. Further, the windshield is provided with a portion for second lenses.

Conventionally, ordinary prescription eyeglasses can only be converted to sunglasses by providing tint to the prescription lenses, or by attaching a color plate on the outside of the lenses. According to the windshield eyeglasses offered by the present invention, the windshield between the user's face and the lenses can easily accommodate second lenses. The second lenses can be sunglass lenses or prescription lenses.

When sunglass lenses are used on the outside and prescription lenses are on the inside, the prescription lenses are less visible from outside, resulting in improved appearance. Further, since the windshield is detachable, the eyeglasses can be used as ordinary sunglasses.

The second lenses can be fixed in the windshield, or detachable therefrom. When the second lenses are detachable, prescription lenses which serve a specific purpose can be selected and easily mounted.

Further, the windshield can also be fixed or detachable with respect to the lenses and/or the frame.

An invention disclosed in Claim 19 is the windshield which is integrally formed with nose pads.

The nose pads are placed on the laterally inward side of the medial angles of eyes, and contacted to the nose surface, determining the distance between the lenses and the user's eyes. Further, the nose pads are located closely to the places where the right and left windshield portions according to the present invention are provided. By forming the nose pads integrally with the windshield, simplification can be achieved not only in structure but also in manufacturing process. Further, by offering a variety in the height and shape of the nose pads provided on the windshield, adjustment becomes possible in accordance with the face features as well as the distance between the eyes and the lenses.

The nose pads can also be connected detachably to one or more place of the windshield lenses and the frame.

The invention disclosed in Claim 20 relates to a wind shielding method for a pair of eyeglasses, comprising a provision of a windshield ranging from the laterally inward side of the face to an upper intermediate portion and to a lower intermediate portion on the edges of the eyeglass lenses or frame for sealing a gap between the edge and the face of a user, thereby preventing airflow from the laterally central area to the outward sides of the face from entering a space between the eyeglass inner surface and the user's face.

When moving forward, with the face orienting ahead, the airflow which hits the face is divided by the nose ridge in right and left directions, and then continues to flow along the face. The airflow along the face comes into gaps between the eyeglasses and the face, and adversely affects the eyes. Especially, the airflow moving from medial angles of the eyes towards the lateral angles of the eyes interferes with the flow of tears, causing inflammation and other troubles in the eyes.

The wind shielding method according to the present invention solves the above problems by changing the route of the airflow. By providing the windshield, airflow from the medial angles of the eyes toward the lateral angles of the eyes is reduced, which reduces the problems of dry eyes and inflammation. Further, there is no need for enclosing entirely around the eyes as long as the airflow can be rerouted. Therefore, the sides outward of the lateral angles of the eyes can be opened to the atmosphere for fresh air. This prevents the lenses from being clouded.

The wind shielding method according to the present invention requires the sealing of gaps between the eyeglass frame and user's face, from a laterally central portion of the face to near the lateral angles of the eyes. On the other hand, each person has different face contours. Therefore, it is preferable that adjustment can be made to the distance between the eyeglasses and the face for sealing the gaps. For example, by adjusting the height and shape of the nose pads according to the user, a highly efficient wind shielding effect can be achieved. In addition, it is preferable that the windshield is detachable so that selection can be made in accordance with face characteristics of the user.

BEST MODE FOR CARRYING OUT THE INVENTION

Figure 1:
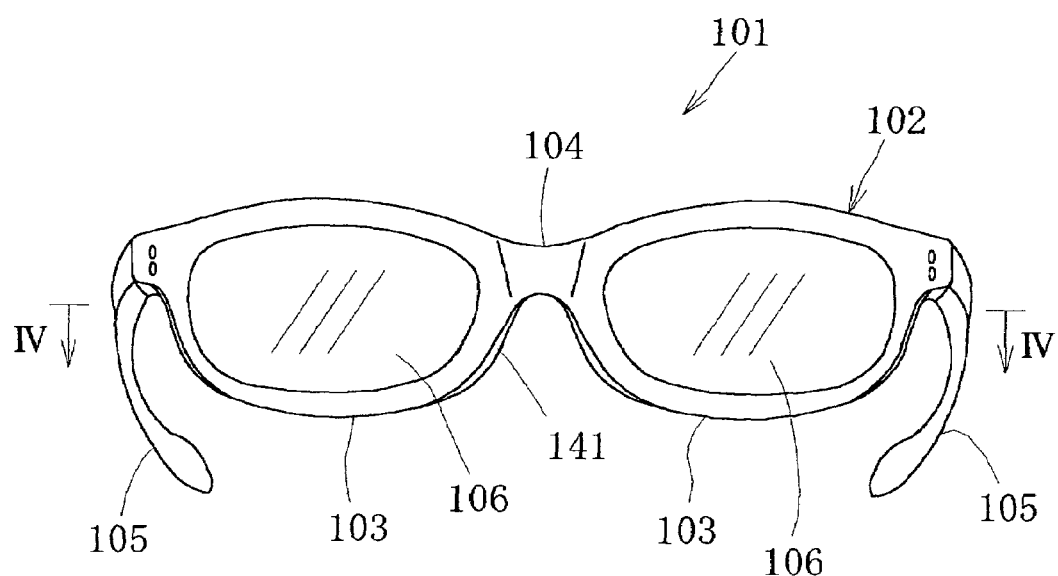
FIG. 1 is a front view of a pair of windshield eyeglasses according to a first embodiment of the present invention.

FIG. 1 through FIG. 5 show a first embodiment of the windshield eyeglasses according to the present invention.

A pair of windshield eyeglasses 101 comprises, like conventional eyeglasses of this kind, a resin frame 102 fitted with a right and a left lenses 106, 106. The frame 102 includes a right and a left rims 103, 103 for holding the lenses 106, 106 respectively, a bridge 104 connecting the rims 103, 103, and a pair of temples 105, 105 connected pivotably by hinges 108, 108 at respective outer ends of the rims 103, 103. According to the present embodiment, the bridge 104 has a back surface integrally formed with nose pads for fitting onto the user's nose thereby supporting the eyeglasses.

Figure 5:
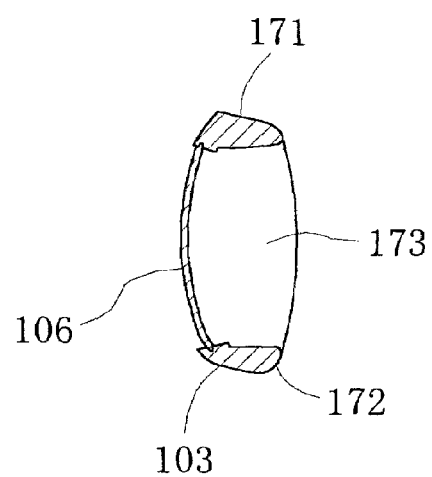
FIG. 5 is a sectional view taken in lines V—V in FIG. 4.
Figure 6:
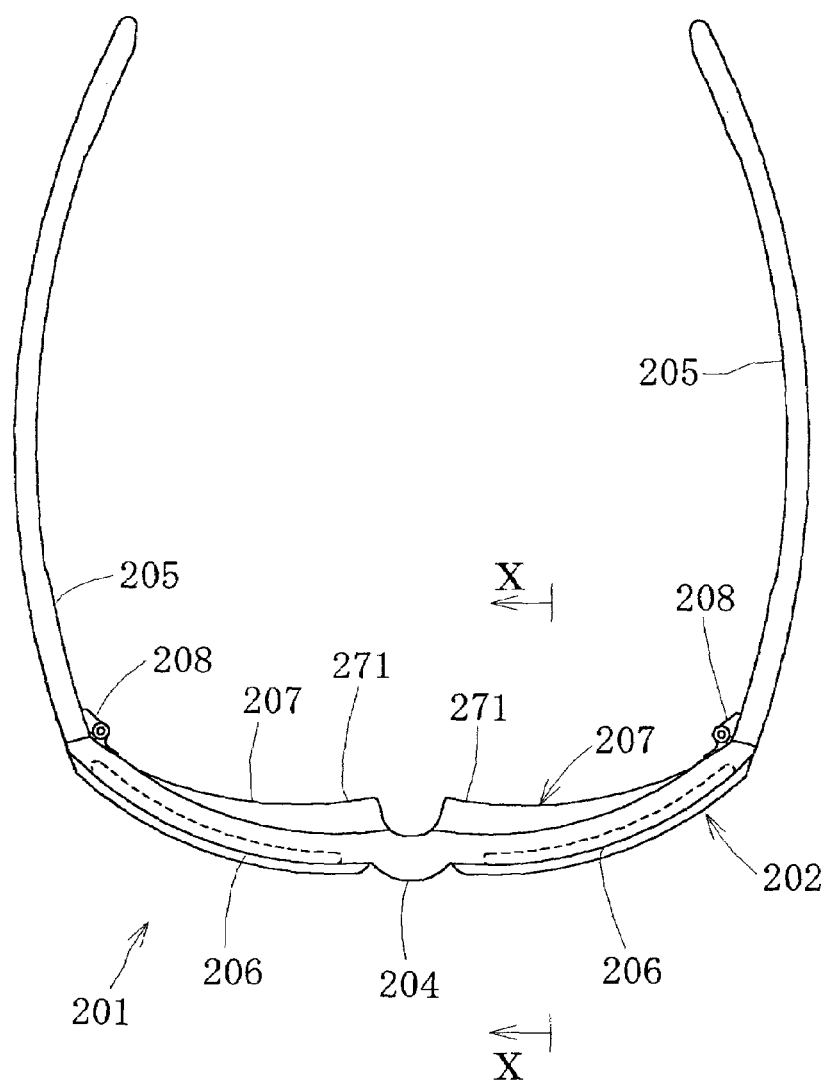
FIG. 6 is a plan view of a pair of windshield eyeglasses according to a second embodiment of the present invention.
Figure 7:
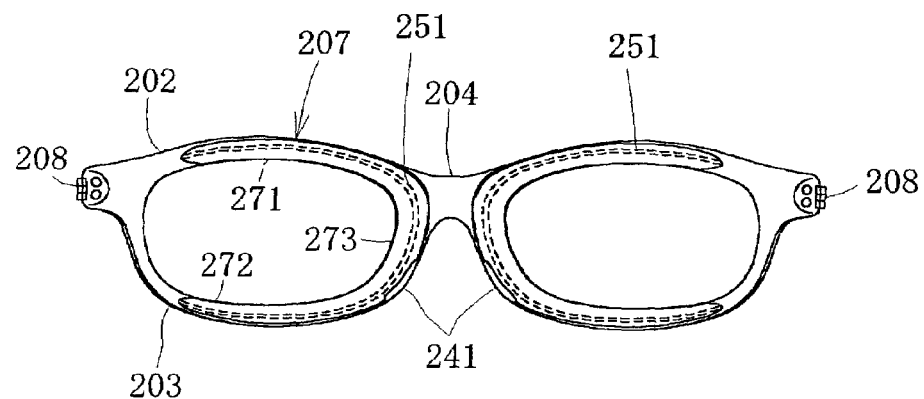
FIG. 7 is a rear view of the windshield eyeglasses in FIG. 6.

On the rims 103, 103, there is provided a pair of windshield portions 107, 107 ranging from a laterally inward side of the face to an upper intermediate portion and to a lower intermediate portion of each rims, extending from the rims toward the user's face so as to seal gaps between the face and the rims 103, 103. The windshield portions 107, 107 are formed integrally with the rims 103, 103. As shown in FIG. 5, each of the windshield portions 107, 107 includes an inner wall 173 extended from the laterally inward side of the rims 103 to surround the medial angle of eye, an upper wall 171 extended from an upper portion of the rim 103, and a lower wall 172 extended from a lower portion of the rim 103. These walls are continuous along the rim 103.

Figure 3:
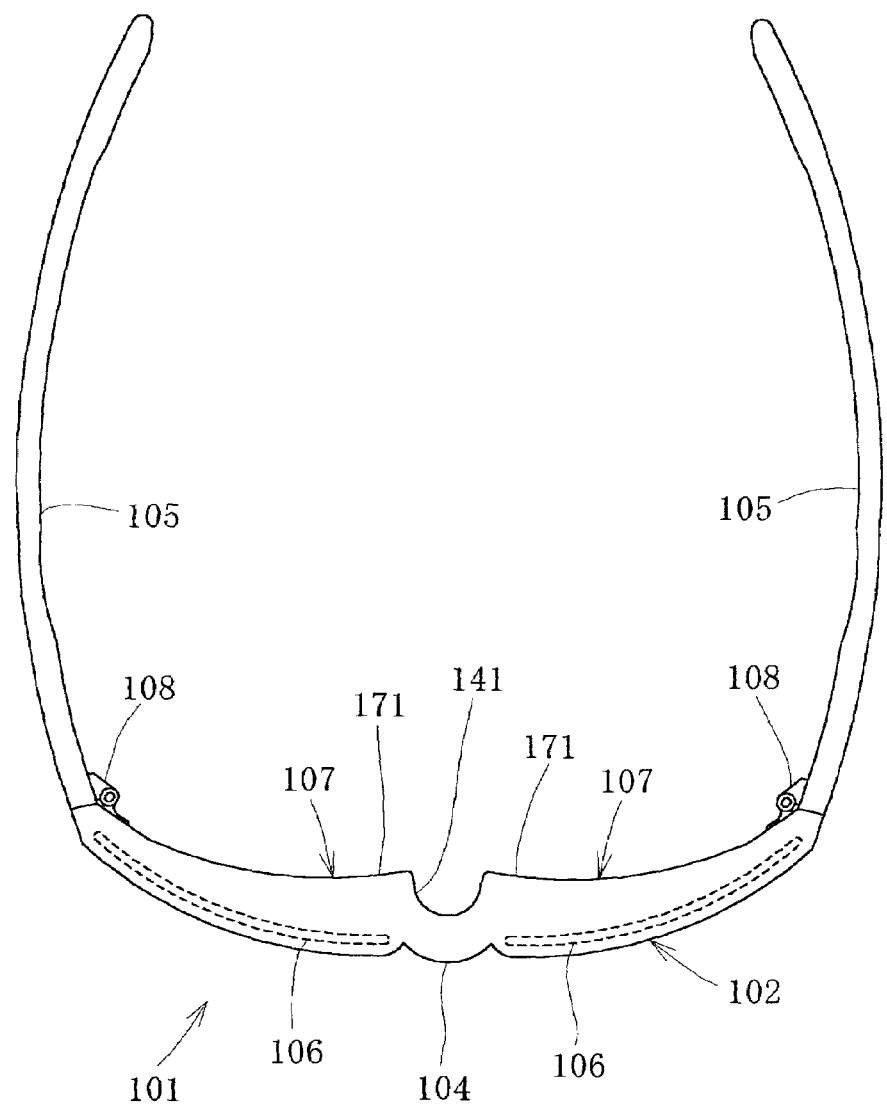
FIG. 3 is a plan view of the windshield eyeglasses in FIG. 1.
Figure 4:
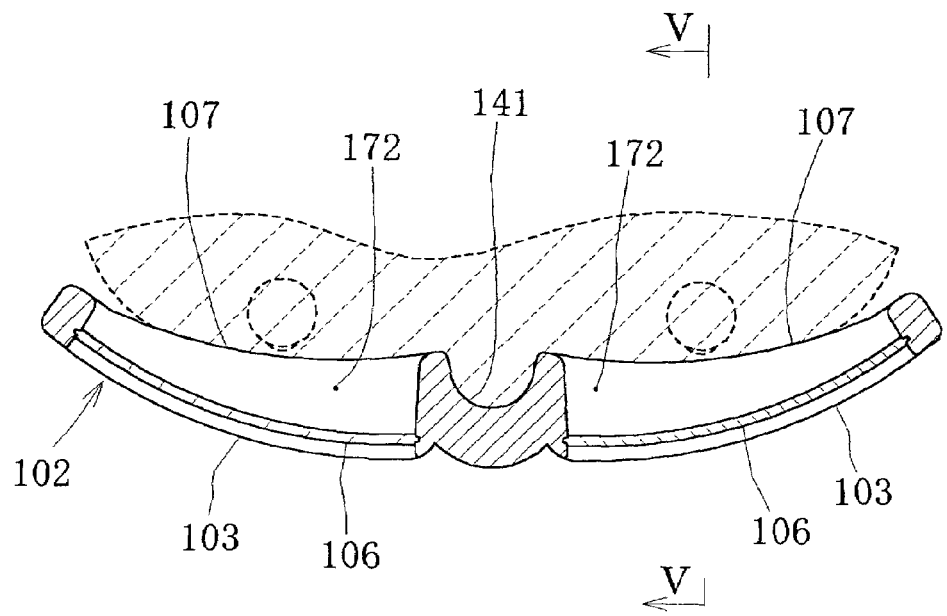
FIG. 4 is a sectional view taken in lines IV—IV in FIG. 1.

As shown in FIG. 3, and FIG. 4, the upper wall 171 and the lower wall 172 are tapered so as to decrease in height outwardly of width, extending laterally to near the user's lateral angle of eye, to fit the user's face and thereby seal any gap between the rim 103 and the face.

The windshield portion 107 makes it possible to seal gaps formed between the eyeglass inner surface and the user's face, from a place further inward of the user's medial angles of the eyes to places above and below the lateral angles of the eyes. This changes airflow along the user's face during high speed movement, preventing the airflow from entering between the eyeglasses and the user's face to affect the eyes. Accordingly, dry eyes and eventual inflammation caused by the disturbed flow of tears is prevented.

Figure 2:
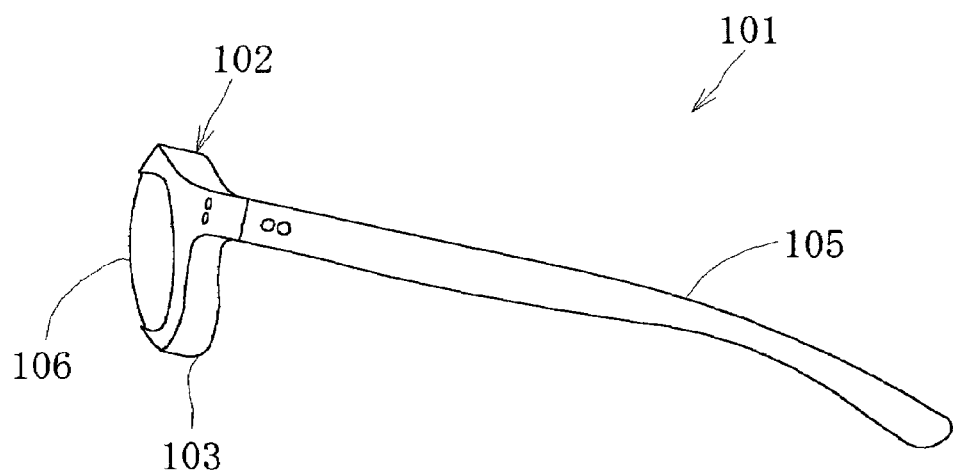
FIG. 2 is a right side view of the windshield eyeglasses in FIG. 1.

On the other hand, as shown in FIG. 1 and FIG. 2, the windshield portion 107 is formed inside of the rims 103, 103. For this reason, the eyeglasses look almost the same as conventional eyeglasses, so the appearance of the eyeglasses is not adversely affected.

Further, the rims 103, 103 are not formed with walls on their laterally outward sides, and exposed to the outer atmosphere. Therefore, air between the eyeglasses and the face is refreshed, preventing the lens inner surfaces from being clouded. Further, the eyeglasses are handy because they can be worn just in the same way as conventional eyeglasses.

FIG. 6 through FIG. 10 show a second embodiment of the present invention.

As shown in these diagrams, a pair of windshield eyeglasses 201 according to the second embodiment has a frame 202 formed of hard resin, and windshields 207 formed of elastic resin and connected to inside surfaces of rims 201 of the frame 202.

Figure 8:
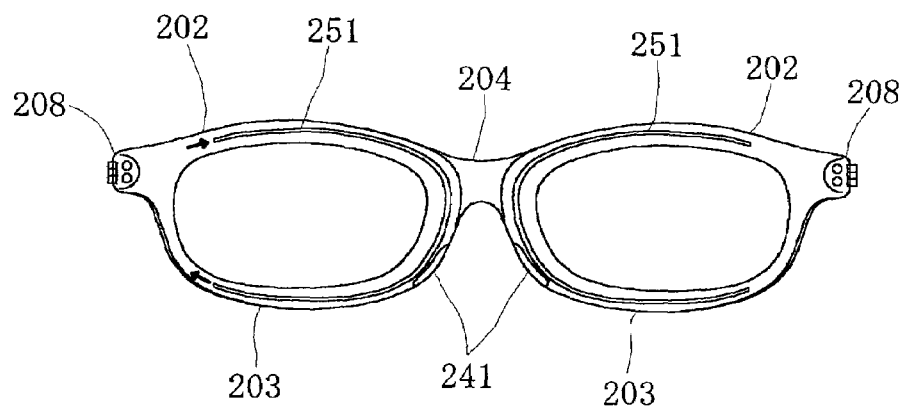
FIG. 8 is a rear view of a frame in FIG. 6.
Figure 9:
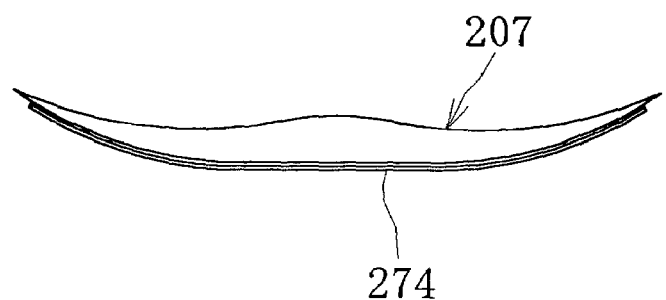
FIG. 9 is a side view of a windshield in FIG. 6.
Figure 10:
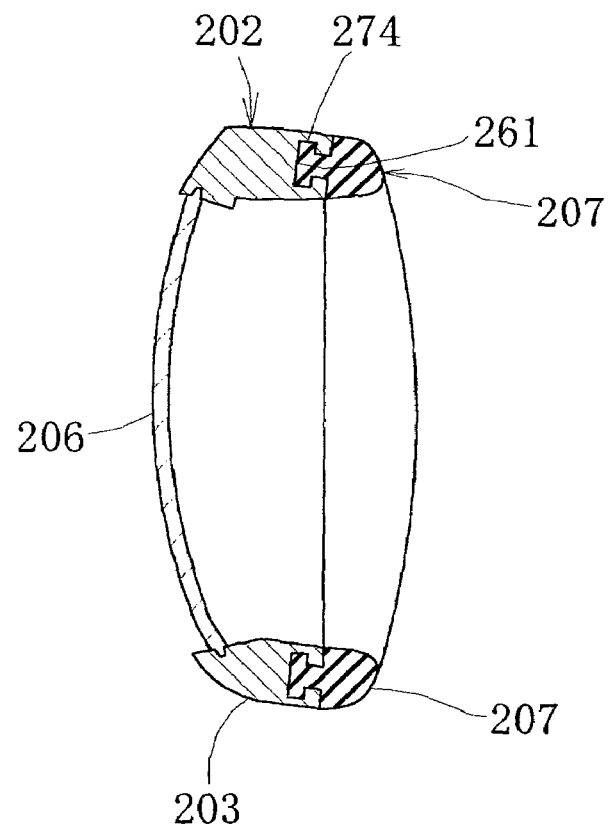
FIG. 10 is a sectional view taken in lines X—X in FIG. 6.

As shown in FIG. 8 through FIG. 10, the rim 203 is provided with an engaging groove 261 ranging from a laterally inward side with respect to the user's face to an upper intermediate portion and to a lower intermediate portion. Ends of the engaging groove open up on the rim surface at the upper and the lower intermediate portions. As shown in FIG. 9, the windshield 207 has a tapered shape, with a center portion being higher, in an integrated shape including the inner wall 173 surrounding the medial angle of the eye, the upper wall 171 extending from the upper portion of the rim 103, and the lower wall 172 extending from the lower portion of the rims 103. The windshield 207 has a fitting face formed with an engaging ridge 274 to fit into the engaging groove 261. By sliding the engaging ridge 274 from an end of the engaging groove 261 in the direction shown by an arrow in FIG. 8, the windshield 207 can be attached to the rim 203 of the frame 202.

The windshield according to the present embodiment is formed of elastic resin, and can deform to fit the contours of the user's face. Thus, it is possible to precisely seal gaps between the rim 203 and the face. Further, it is possible to manufacture various kinds of the windshield for varieties of combination with the frame 302, to match different features of the users or to meet likes and desires of the users. Further, the elastic resin has a gentle, comfortable fit on the user's face.

Figure 11:
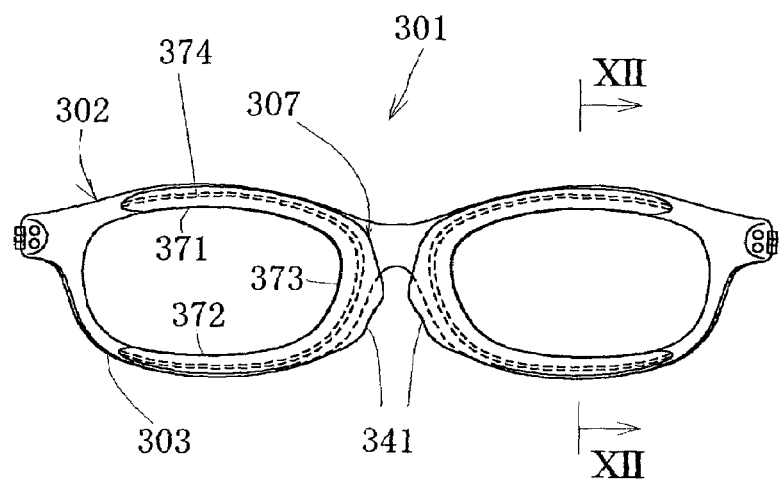
FIG. 11 is a rear view of a pair of windshield eyeglasses according to a third embodiment of the present invention, and is a view corresponding to FIG. 7.
Figure 12:
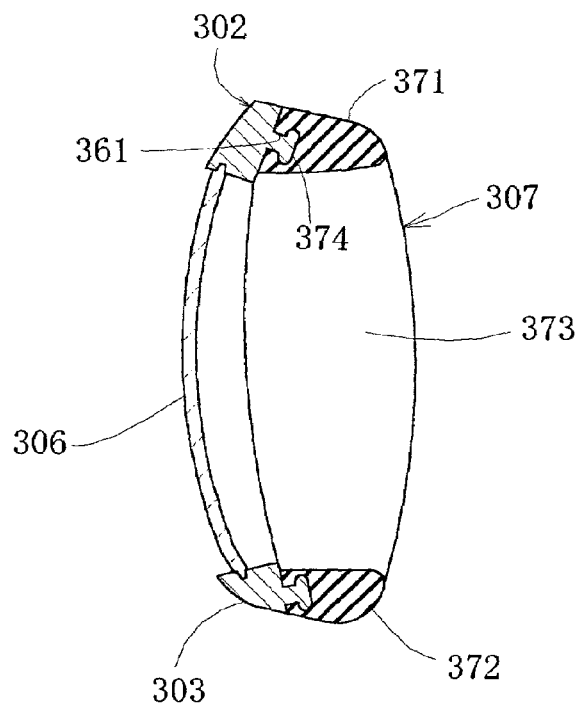
FIG. 12 is a sectional view taken in lines XII—XII in FIG. 11.
Figure 13:
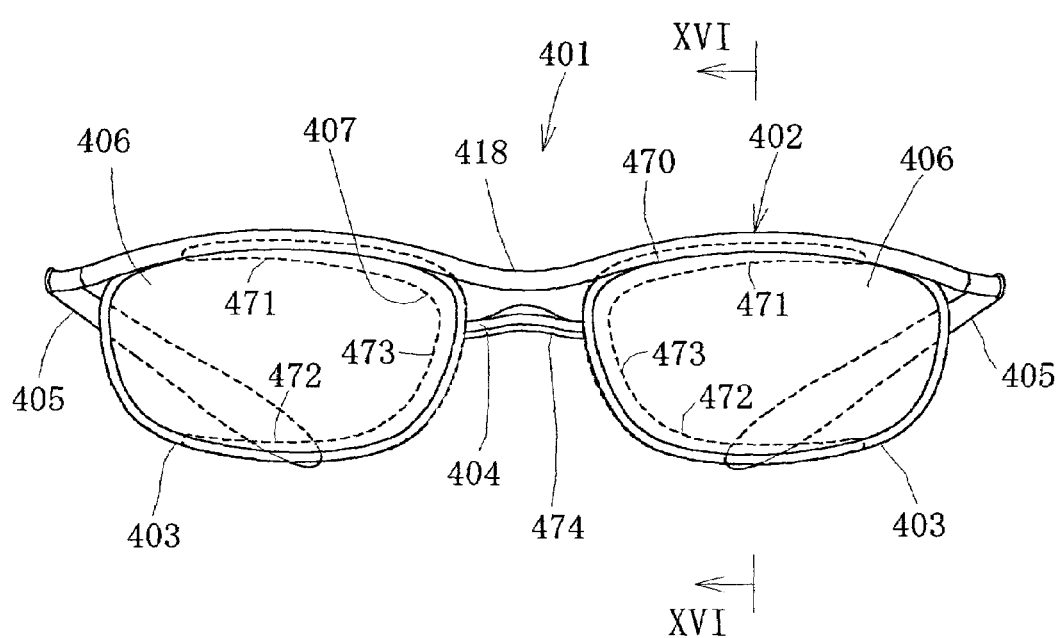
FIG. 13 is a plan view of a pair of windshield eyeglasses according to a fourth embodiment of the present invention.
Figure 14:
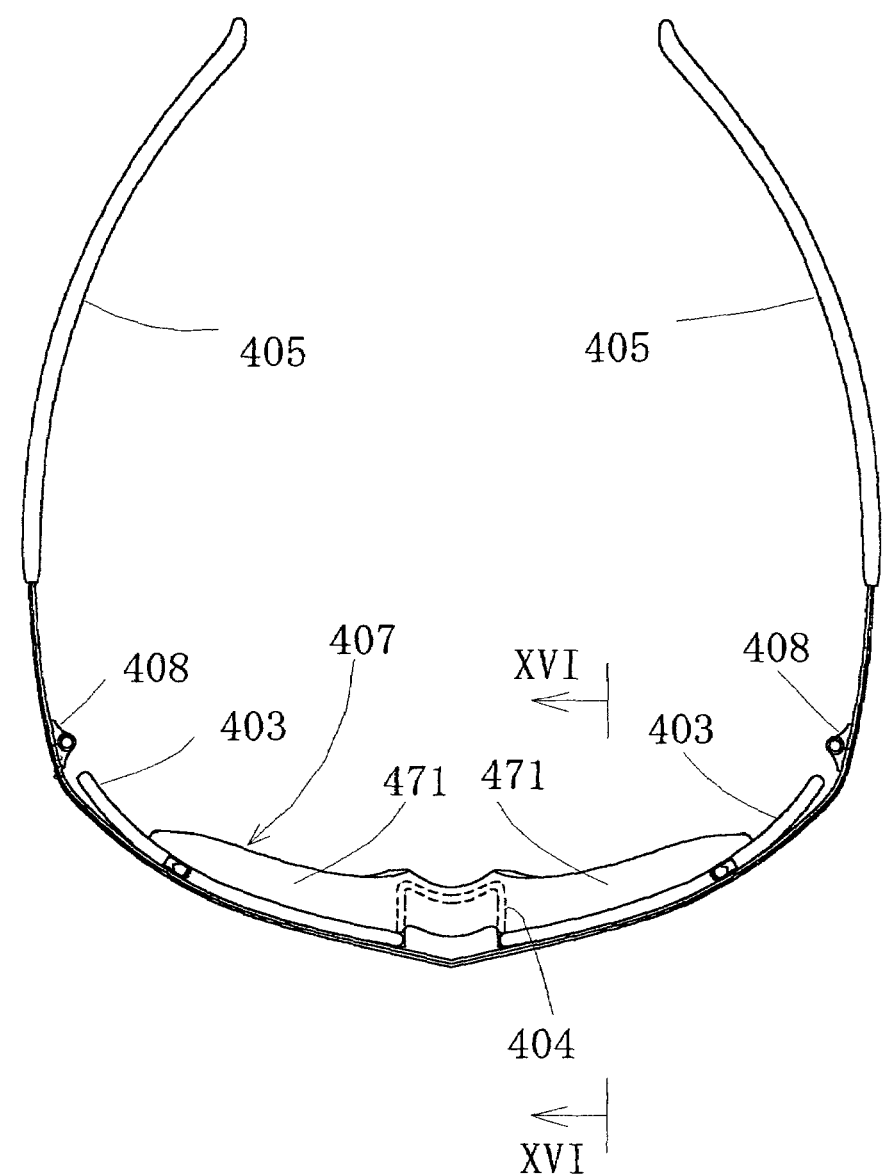
FIG. 14 is a plan view of the windshield eyeglasses in FIG. 13.
Figure 15:
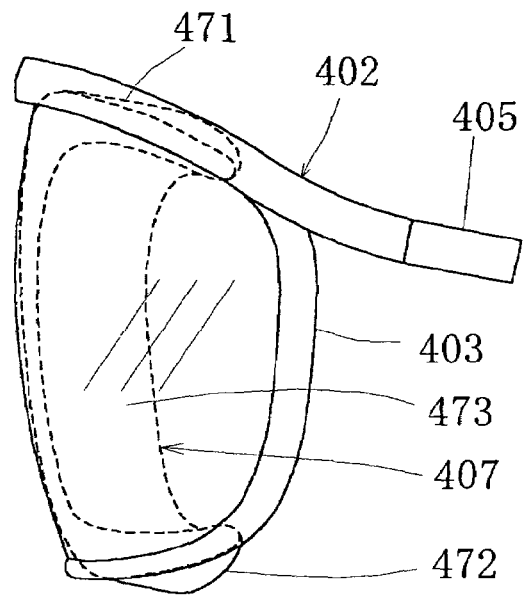
FIG. 15 is a right side view of a primary portion of the windshield eyeglasses in FIG. 13.

FIG. 11 through FIG. 12 show a third embodiment of the present invention.

As is the second embodiment, a pair of windshield eyeglasses 301 according to the third embodiment has a frame 302 formed of hard resin, and windshields 307 formed of elastic resin and connected to inner surfaces of the rims 301 of the frame 302.

As shown in FIG. 12, according to the present embodiment, the rim is formed with an engagement ridge 374 in the inner surface, and the windshield 307 has a fitting face formed with an engaging groove 361. The windshield 307 can be attached to the rims 303 basically in the same way as in the second embodiment.

FIG. 13 through FIG. 22 show a fourth embodiment of the present invention.

As shown in these diagrams, a pair of windshield eyeglasses 401 comprises a metal frame 402, and a right and a left lenses 406, 406 mounted thereon. The frame 402 includes right and left rims 403, 403 holding the lenses 406, 406 respectively, a bridge 404, a top rim 418 connecting the rims 403, 403, and a pair of temples 405, 405 connected pivotably by hinges 408, 408 at respective outer ends of the top rim 418. According to the present embodiment, the bridge 404 is provided by a single-peak bridge.

The eyeglasses 401 according to the present embodiment have a back surface via which a windshield 407 is detachably mounted.

As shown in FIG. 17 through FIG. 22, the windshield 407 is integrally formed of resin, including inner walls 473 to surround the medial angles of the eyes, upper walls 471 extended from an upper portion of each rim 403, and lower walls 472 extended form a lower portion of each rim 403. These walls are formed to be continuous along the edges of the rims 403 or lenses 406. The right and left walls are integrated with each other via a connecting portion 474.

Figure 17:
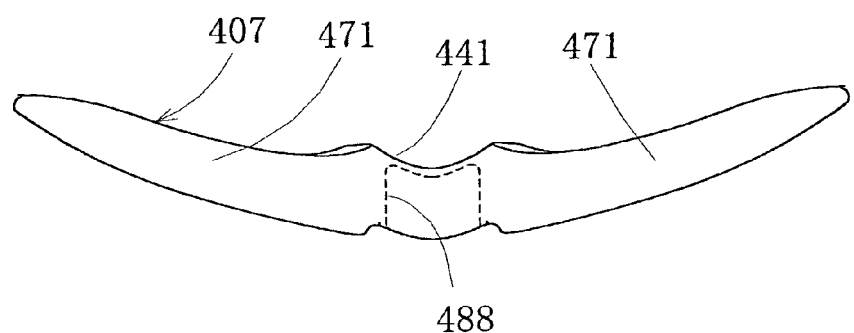
FIG. 17 is a plan view of the windshield in FIG. 13.
Figure 18:
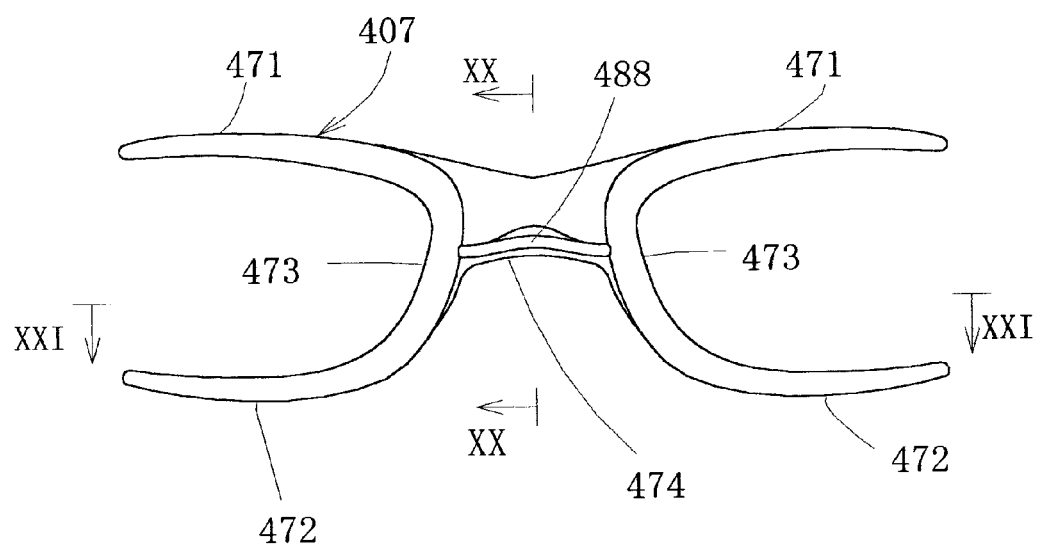
FIG. 18 is a front view of the windshield in FIG. 13.
Figure 19:
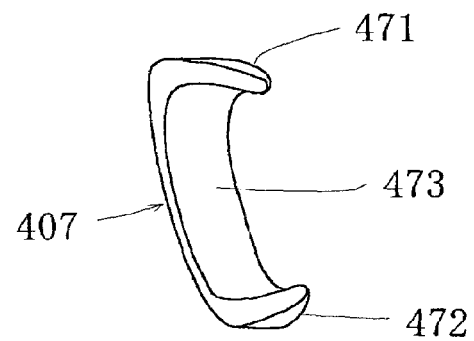
FIG. 19 is a right side view of the windshield in FIG. 13.
Figure 20:
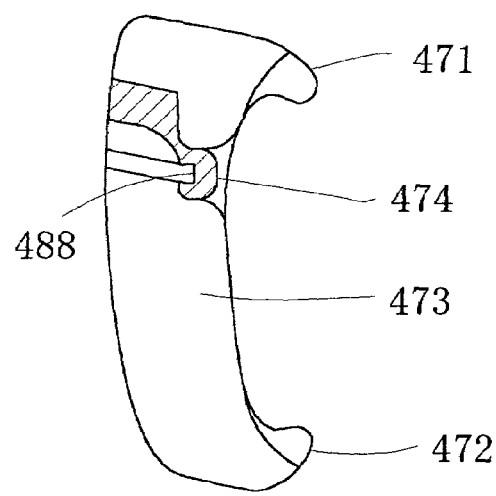
FIG. 20 is a sectional view taken in lines XX—XX in FIG. 18.
Figure 21:
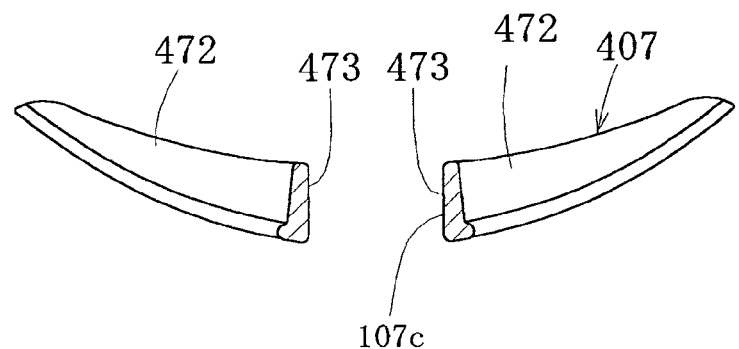
FIG. 21 is a sectional view taken in lines XXI—XXI in FIG. 18.

The connecting portion 474 is formed to fit along the bridge 404 of the eyeglasses 401, with the outer surface formed with a connecting groove 488 for catching the bridge 404. As shown in FIG. 17 and FIG. 18, the connecting groove 488 has a U-shaped section along the connection portion 474 and the outer surface of the inner walls 473, so as to flexibly fit and hold the bridge 404.

Figure 16:
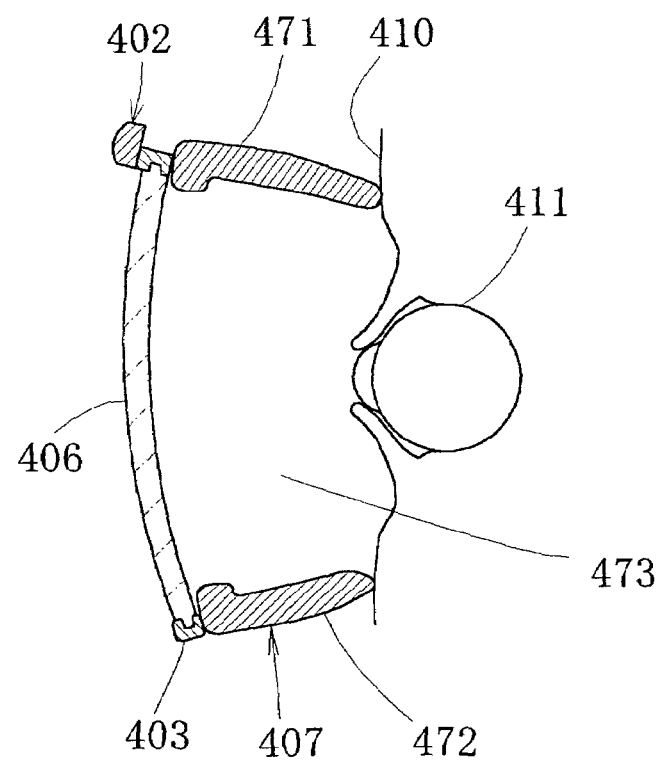
FIG. 16 is a sectional view taken in lines XVI—XVI in FIG. 13.
Figure 22:
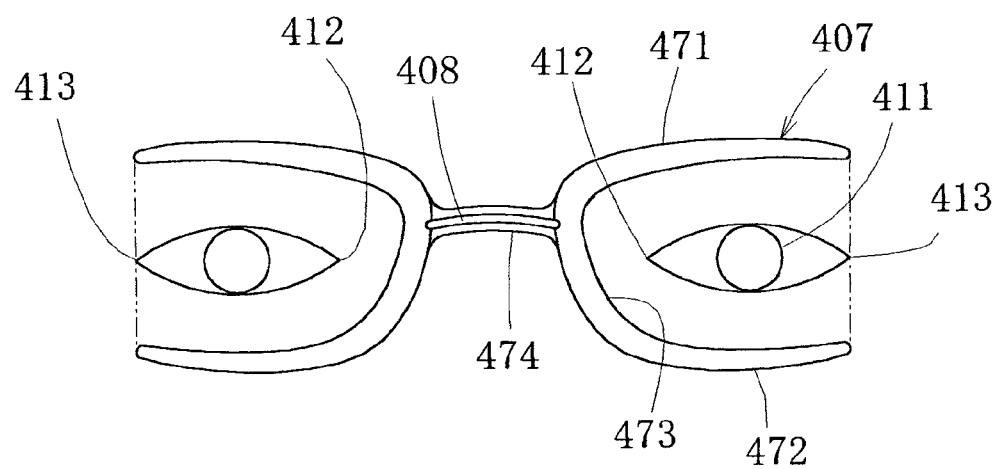
FIG. 22 is a diagram illustrating positional relationships between a windshield and the eyes.

As shown in FIG. 22, the upper walls 471 and the lower walls 472 extend to surround as far as near the user's lateral angles of the eyes 413 from above and below. Further, as shown in FIG. 16, the walls are arranged to seal gaps between the user's face 410 and the rims 403 or the lenses 406, ranging from a laterally intermediate portion to an upper intermediate portion and to a lower intermediate portion of the rims 403.

By attaching the windshield 407 to a pair of eyeglasses, the same advantages as described for the first embodiment are offered.

Further, according to the present embodiment, the windshield 407 is detachable. Thus, it is possible to offer various kinds of the windshield to match different features of the users or to fit different shapes of the eyeglasses. This enables to offer windshields which have highly effective wind shielding capabilities.

Further, when the windshield 407 is detached, the eyeglasses 401 can be used as ordinary eyeglasses. There is less likelihood of interfering with the esthetic design of the eyeglasses. In addition, since the windshield 407 is attached inside the eyeglasses 401, there is no likelihood that strong airflow which hits the user's face will vibrate or dislocate the windshield. Since there is enough space between the lens inner surface and the user's face, it is not likely that the cilia would make contact with the lenses.

Figure 23:
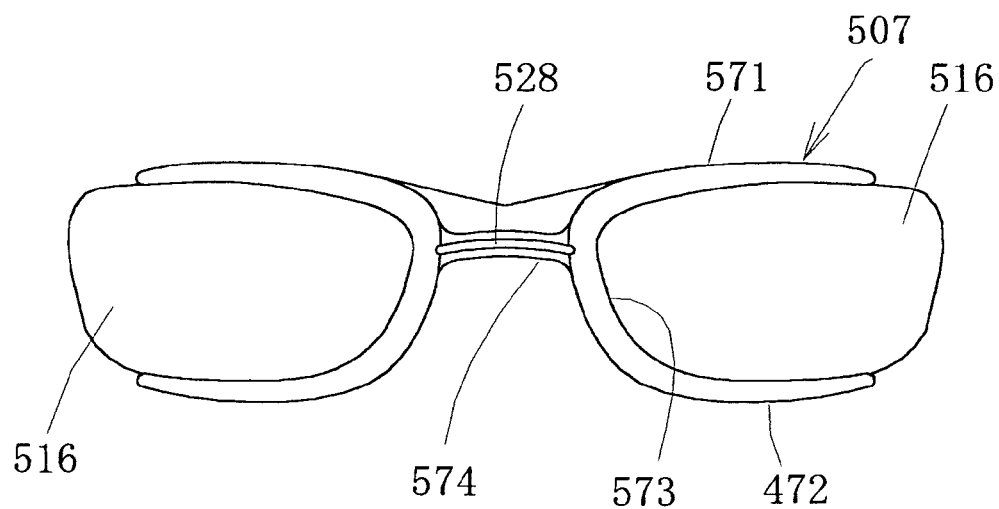
FIG. 23 is a front view of a pair of windshield eyeglasses according to a fifth embodiment of the present invention.
Figure 24:
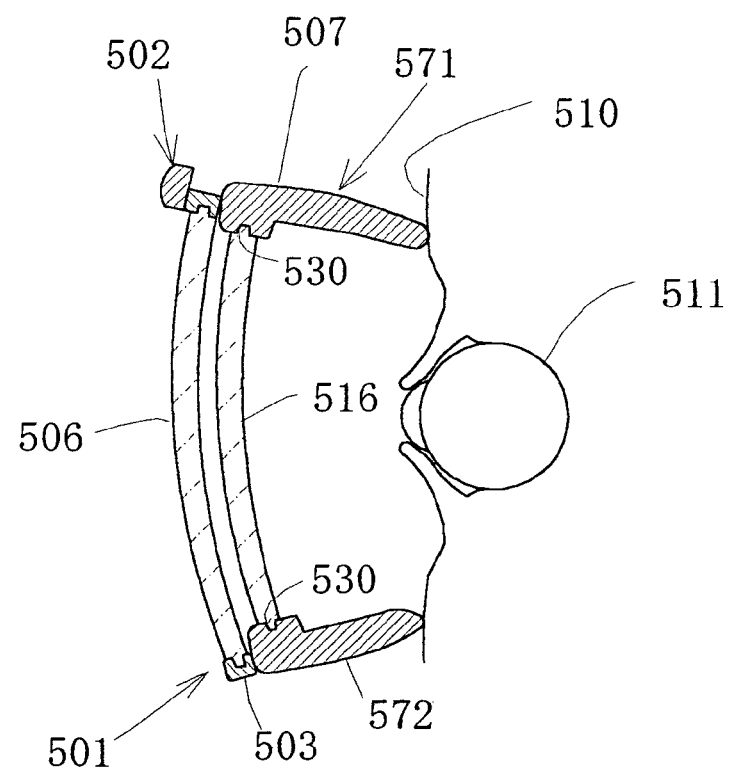
FIG. 24 is a diagram illustrating the windshield in FIG. 23 as mounted onto a pair of eyeglasses, sowing a section corresponding to FIG. 16.

FIG. 23 through FIG. 24 show a fifth embodiment of the present invention.

A windshield 507 according to the present embodiment is the windshield 407 according to the fourth embodiment capable of incorporating second lenses 516 inside the eyeglasses. It should be appreciated that no description will be made for a pair of eyeglasses 501 itself since it is the same as the second embodiment.

As shown in FIG. 23 and FIG. 24, the windshield 507 is integrally formed of a resin, including a right and a left wall portions fitted along edges of respective rims 503 or lenses 506 of the eyeglasses 501, and a connecting portion 574 which connects the wall portions.

The right and the left wall portions of the windshield 507 each include an inner wall 573 fitted to an inner edge of the rim 503 or lens 506, an upper wall 571 fitted to an upper edge of the rim 503 or lens 506, and a lower wall 572 fitted to a lower edge of the rim 503 or 506. These walls are continuous with each other along the rims 503 or the lenses 506.

The connecting portion 574 has a shape to follow along the bridge as in the fourth embodiment, and has an outer surface formed with a connecting groove 528 for holding the bridge. The connecting groove 528 is along the outer surface of connection portion 574 and inner walls 573, and can elastically hold the bridge.

The upperwalls 571 and the lowerwalls 572 surround the user's eyes as far as above and below the lateral angles of the eyes, as in the fourth embodiment shown in FIG. 22. The walls seal gaps between the user's face and the rims 503 or lenses 506 over the ranges from a laterally inward side of the rims 503 to an upper intermediate and a lower intermediate portions of each rim.

According to the present embodiment, as shown in FIG. 24, grooves 530 are provided in inner edges of the upper wall 571 and the lower wall 572. These grooves 530 fit around a peripheral edge of a prescription lens 516 thereby holding the lens. On the other hand, the outer lens is a colored sunglass lens capable of shielding ultraviolet rays.

By using the above arrangement, it becomes possible to make the prescription lens 516 invisible from the outside, thereby to give the same appearance as wearing ordinary sunglasses. Unlike a colored plate attached outside of the lenses, the present arrangement does not affect the esthetic design of the eyeglasses. Further, by removing the windshield 507, the glasses can be used as ordinary sunglasses.

It should be noted here that the second lenses 516 may be fixed in the windshield 507 or detachable therefrom. Further, the lenses 506 may be prescription lenses while the second lenses are sunglass lenses.

Figure 25:
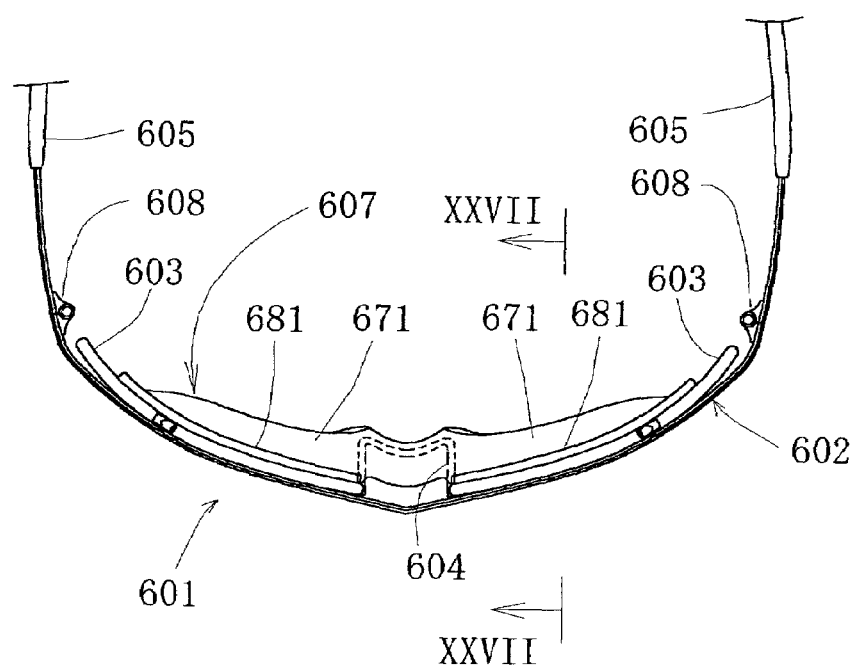
FIG. 25 is a plan view of a pair of windshield eyeglasses according to a sixth embodiment of the present invention.
Figure 26:
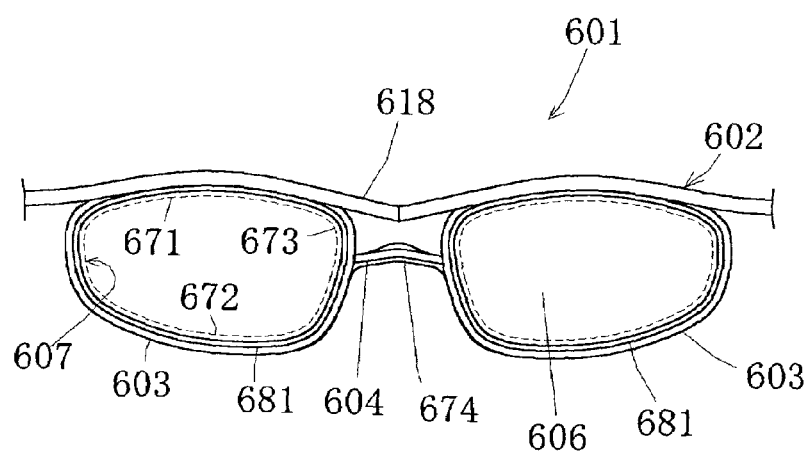
FIG. 26 is a plan view of the windshield eyeglasses in FIG. 25.
Figure 27:
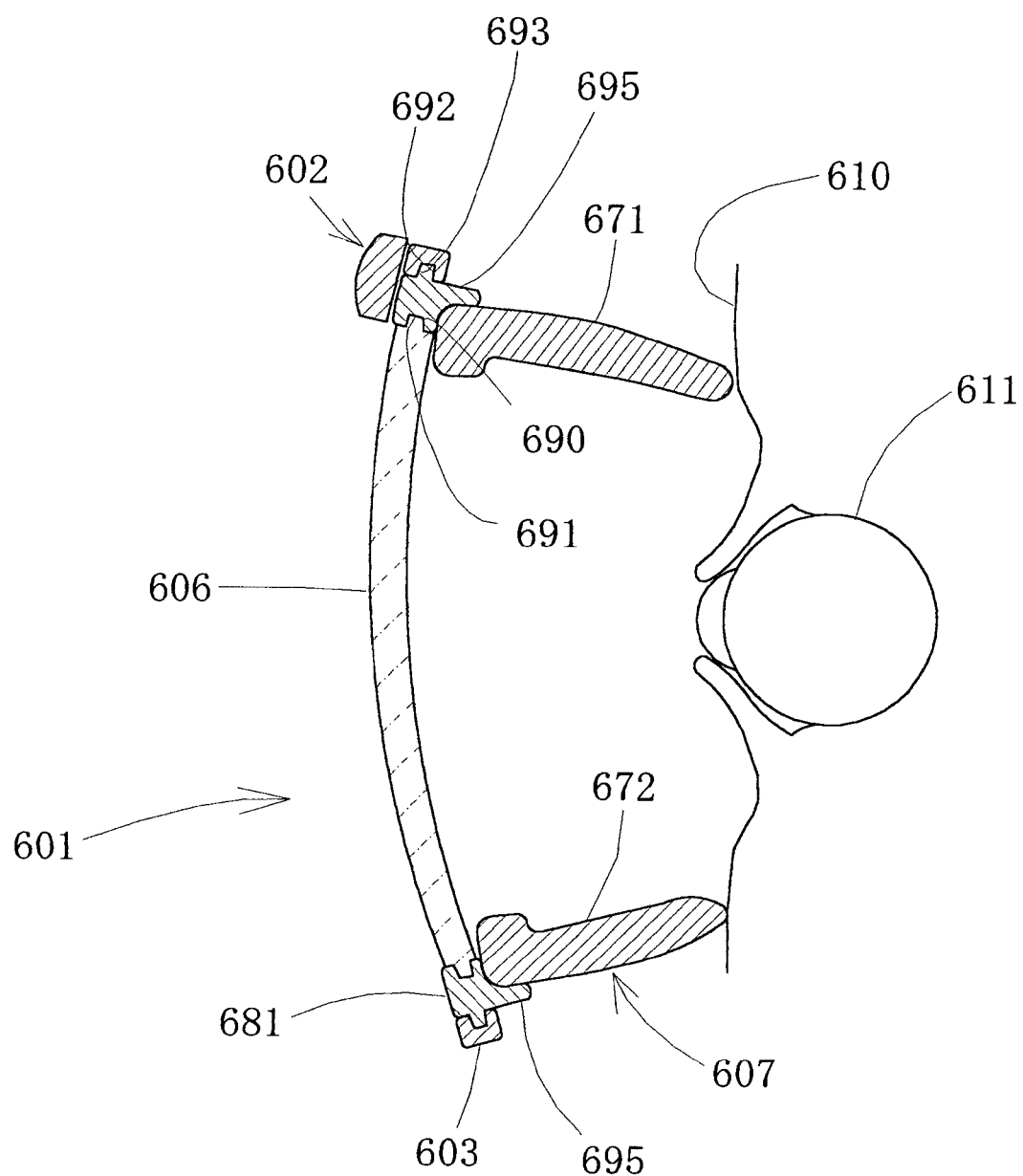
FIG. 27 is a sectional view taken in lines XXVII—XXVII in FIG. 25.

FIG. 25 through FIG. 27 show a sixth embodiment of the present invention.

The present embodiment uses a windshield 607, which is identical with those in the fifth embodiment, and thus will not be described here again.

According to the present embodiment, as shown in FIG. 25 and FIG. 26, a middle frame 681 is provided between a rim 603 of the frame 602 and each lens 606. As shown in FIG. 27, the middle frame 681 has an inner side surface formed with an engaging groove 691 fitted by an engaging ridge 690 of the lens 606. Further, the middle frame 681 has an outer side surface formed with an engaging ridge 692 fitted into an engaging groove 693 of the rim 603. The lens 606 is held by the rim 603 via the middle frame 681.

As shown in FIG. 27, the middle frame 681 is formed with an extension 695 on a side closer to the user's face so as to cover the outer edge of the windshield. The extension 695 allows the edge of the windshield 607 to be fitted inside the extension 695. This covers any gaps between the windshield 607 and the rim 603, preventing airflow from coming in.

Further, since the extension 695 is formed in the middle frame 681, the lens and the frame can be manufactured in exactly the same way as conventionally. In addition, the extension can be varied to fit different shapes of the windshield.

Figure 28:
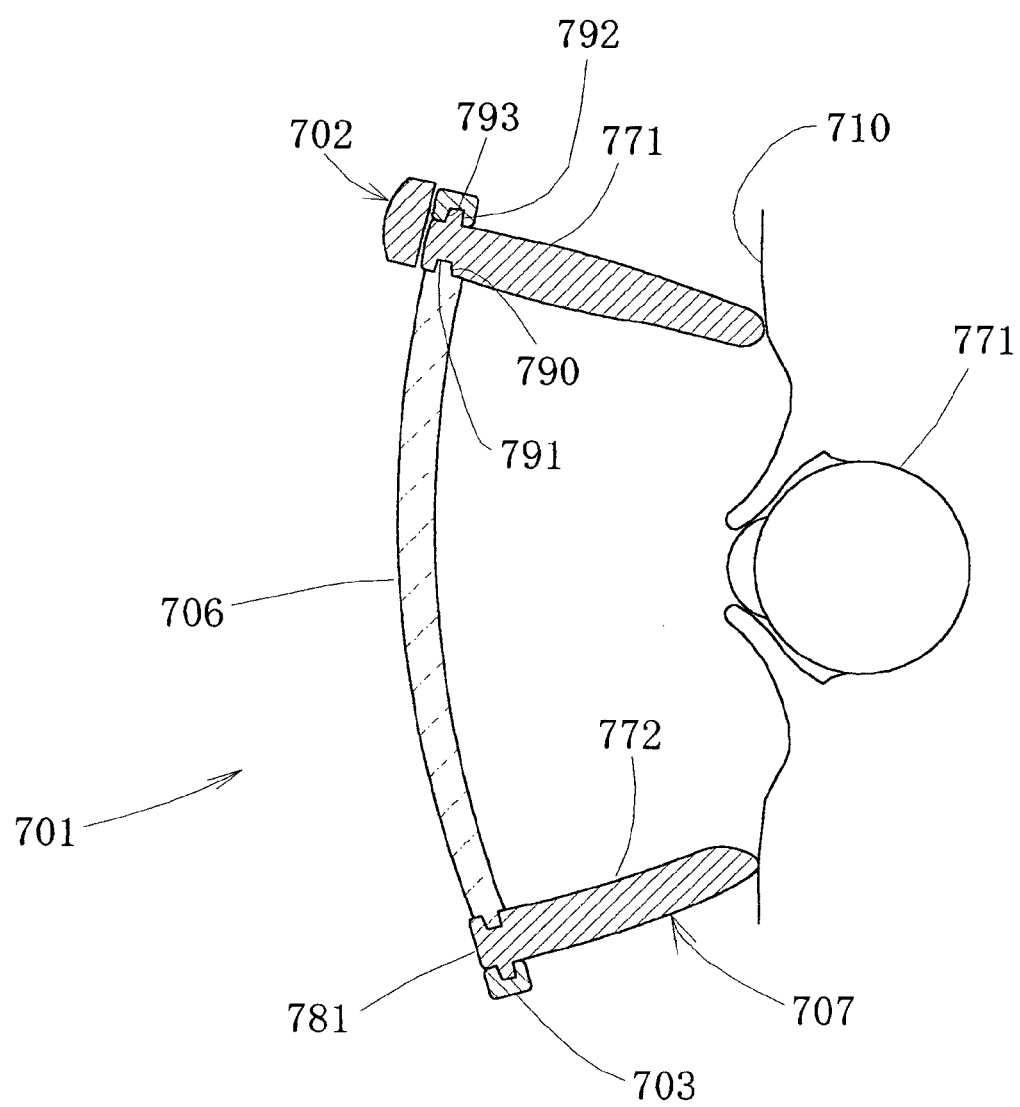
FIG. 28 is a sectional view of a seventh embodiment of the present invention, and is a view corresponding to FIG. 27.

FIG. 28 shows a seventh embodiment of the present invention.

The present embodiment uses a pair of windshield eyeglasses 701 comprising a frame 702 and a windshield 707, which are identical with those according to the fifth embodiment, and thus will not be described here again.

According to the present embodiment, as shown in FIG. 28, the middle frame according to the sixth embodiment is integrally formed with the windshield 707. The middle frame 781 has an inner side surface formed with an engaging groove 791 fitted by an engaging ridge 790 of a lens 706. Further, the middle frame 781 has an outer side surface formed with an engaging ridge 792fitted into an engaging groove 793 of a rim 703. The lens 706 is held by the rim 703 via the middle frame 781.

As in the previous embodiments, the windshield 707 includes a set of an inner wall 773 surrounding the medial angle of eye, an upper wall 771 extending from an upper edge of the rim 703, and a lower wall 772 extending from a lower edge of the rim 703, on each of the right and the left sides. The walls provide an enclosure ranging from the laterally inward side of the medial angles of the eyes to above and below the lateral angles of the eyes, and seal gaps between the user's face and the rims 703 or lenses 706.

By providing the windshield 707 integrally with the middle frames 781, the lenses and the frame can be manufactured in exactly the same way as conventionally. In addition, the windshield can be varied to fit different features of users.

Figure 29:
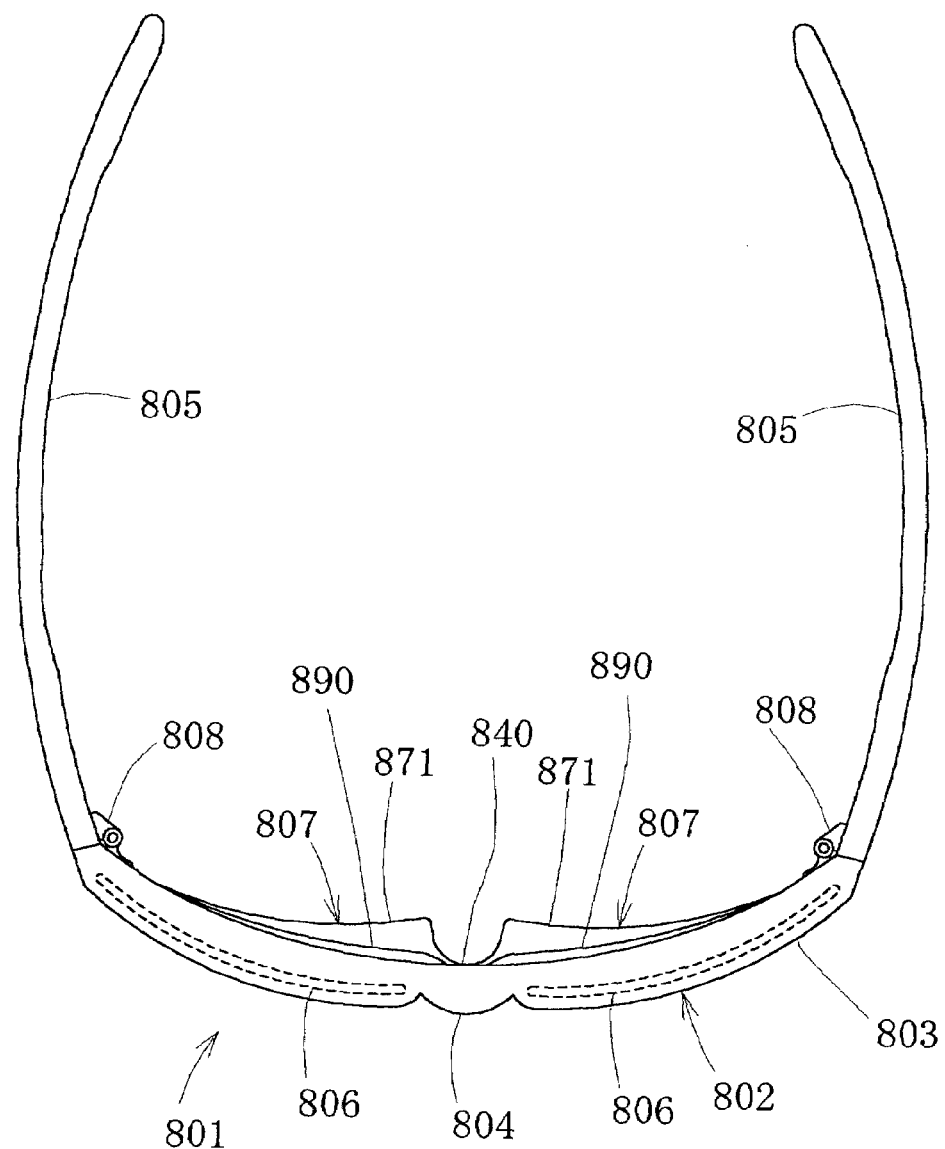
FIG. 29 is a plan view of a pair of windshield eyeglasses according to an eighth embodiment of the present invention.
Figure 30:
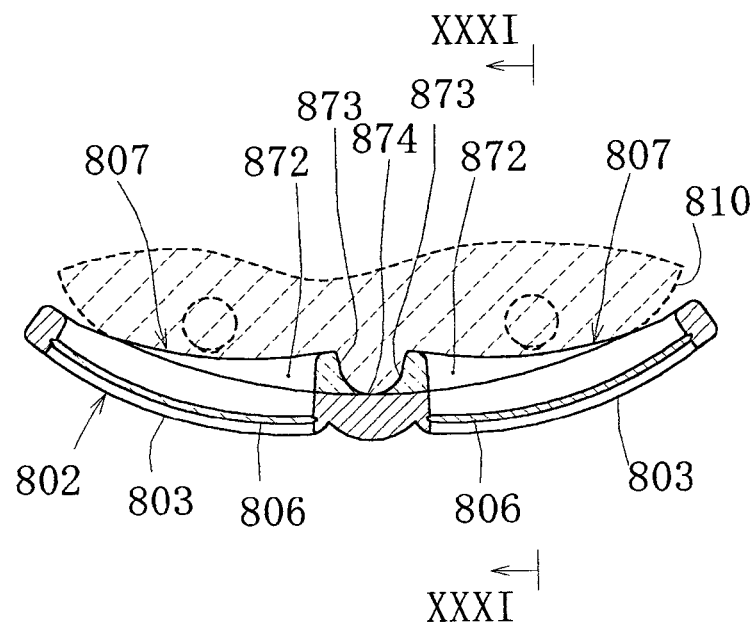
FIG. 30 is a view showing a horizontal section of the windshield eyeglasses in FIG. 29, and is a view corresponding to FIG. 4.
Figure 31:
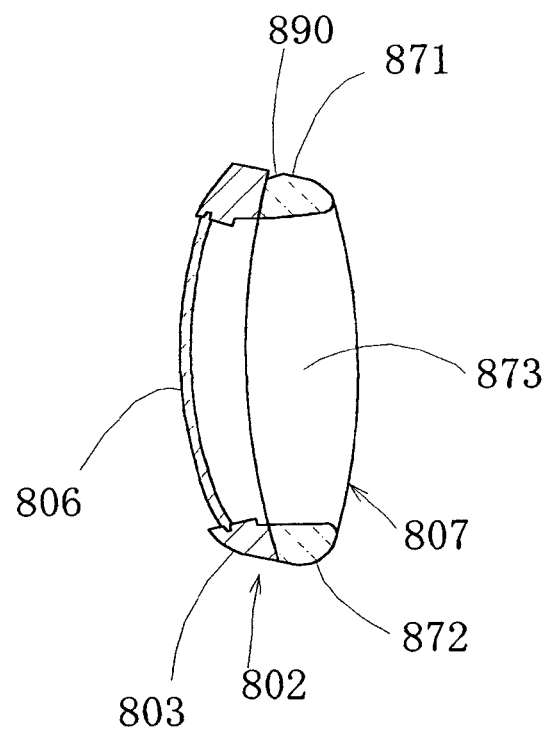
FIG. 31 is a sectional view taken in lines XXXI—XXXI in FIG. 30.

FIG. 29 through FIG. 31 show an eighth embodiment of the present invention.

A pair of windshield eyeglasses 801 according to the present embodiment includes a windshield 807 which is the windshield according to the first embodiment, formed integrally with a frame 802 but in a different color from the color of the frame. Preferably, the frame 802 is made of colored resin while the windshield 807 integrated therewith is made of transparent resin.

Further, according to the present embodiment, a bordering groove 890 is formed along an upper edge border between the frame 802 and the windshield 807.

The windshield 807 formed of transparent resin makes the windshield less noticeable, alleviating an impression that the frame main body is thick. This helps improve esthetic design. Further, the windshield allows light to come inside the space behind the eyeglasses, creating a look and feel similar to those of conventional eyeglass frames.

By forming the bordering groove 890, it becomes possible to reduce visual impact of the windshield on the appearance of the eyeglasses. Further, combination of the transparent windshield 807 and the bordering groove 890 causes light to refract in the bordering groove, creating a prism effect which represents a unique frame design unfound before. The bordering groove 890 is preferably formed at least along the upper edge of the windshield, since the upper edge of the windshield is the most eye-catching region.

The present invention is not limited to the embodiments so far described.

In the embodiments, the present invention is applied to a type of eyeglasses in which a frame includes two rims connected with each other by a bridge, and right and left lenses are held individually in the rims respectively. However, the present invention is also applicable to eyeglasses in which the right and left lenses are formed in a single piece.

Further, according to the embodiments, lenses are held by rims along peripheral edges. However, the present invention is also applicable to eyeglasses in which lenses are not held by the rims but connected directly by a bridge or a top rim. In this case, the windshield can be attached to an edge of the lenses. For example, the windshield can be formed of elastic resin and attached to the edge of the rims using adhesive or fitting means. Alternatively, the windshield may be attached to the nose pads.

According to the sixth embodiment, an extension to fit over an outer edge of the windshield was formed around each rim. Alternatively, elimination of gaps between the windshield and the frame can be achieved by different means provided along the edges of the rims or lenses for fitting with the edge of the windshield.

According o the fifth embodiment, a sunglass lens and a prescription lens are used. Alternatively, both may be prescription lenses.

Further, according to the fifth embodiment, the second lenses are held by a windshield which is detachable from the eyeglass main body. Alternatively, there can be an arrangement that the windshield according to the first embodiment which is integrated with the eyeglasses may be formed with a lens holding grooves so that the second lenses can be held detachably.

The invention claimed is:

1. A pair of windshield eyeglasses comprising lenses and a frame for holding the lenses,
wherein each of the lenses or the frame includes an edge formed with a windshield for sealing a gap between the edge and a face of a user at only upper, lower, and laterally inward sides of the lenses or frames, the windshield extending from the edge and ranging from laterally inward side of the face to an upper intermediate portion and to a lower intermediate portion of the edge without ranging to laterally outward side of face.

2. The windshield eyeglasses according to claim 1, wherein the windshield includes a right and a left windshield portions for partially surrounding the right and left eyes respectively, ranging from the laterally inward side of medial angles of eyes to above and below the lateral angles of the eyes.

3. The windshield eyeglasses according to claim 2, wherein the right and the left windshield portions are formed integrally and continuously with each other.

4. The windshield eyeglasses according to claim 1 or claim 2, wherein the frame is formed of hard resin or metal whereas the windshield is formed of elastic resin.

5. The windshield eyeglasses according to claim 1 or claim 2, wherein the eyeglasses further include a middle frame between an outer perimeter of each lens and the frame which holds the lenses, the windshield being provided on the middle frame.

6. The windshield eyeglasses according to claim 1, wherein the lenses respectively serving the right and the left eyes are provided in a form of a single piece, the windshield being formed integrally along the piece or the frame which holds the piece.

7. The windshield eyeglasses according to claim 1 through claim 6, wherein the windshield is formed integrally with nose pads.

8. A pair of windshield eyeglasses comprising lenses and a frame for holding the lenses,
wherein each of the lenses or the frame includes an edge formed with a windshield for sealing a gap between the edge and a face of a user, the windshield extending from the edge and ranging from laterally inward side of the face to an upper intermediate portion and to a lower intermediate portion of the edge, wherein the frame is formed of colored resin whereas the windshield is formed of transparent resin, the frame and the windshield being formed integrally with each other, the frame and the windshield sharing a border area along which a bordering groove is formed.

9. A wind shielding method for a pair of eyeglasses, comprising a provision of a windshield ranging from the laterally inward side of the face to an upper intermediate portion and to a lower intermediate portion on edges of eyeglass lenses or frame without ranging to laterally outward side of face, for sealing a gap between the edge and the face of a user at only upper, lower, and laterally inward sides of the lenses or frame, thereby preventing airflow from the laterally central region of the face toward the laterally outward sides of the face from entering a space at the laterally central region of the face between the eyeglass inner surface and the user face.

* * * * *